United States Patent
Amerik et al.

[11] Patent Number: 6,096,853
[45] Date of Patent: Aug. 1, 2000

[54] SYNTHESIS OF PHENOLIC MONOMERS CONTAINING IMIDE OR DIIMIDE MOIETIES AND HIGH HEAT CARBONATE POLYMERS PREPARED THEREFROM

[75] Inventors: Valentina Amerik, Moscow, Russian Federation; Theodorus L. Hoeks, Bergen op Zoom, Netherlands; Parfait Jean Marie Likibi, Newburgh; Mark Nelson, Mt. Vernon, both of Ind.

[73] Assignee: General Electric Company, Schnenctady, N.Y.

[21] Appl. No.: 09/217,026

[22] Filed: Dec. 21, 1998

[51] Int. Cl.$^7$ .................................................. C08G 64/00
[52] U.S. Cl. ........................................... 528/196; 528/179
[58] Field of Search ...................... 528/179, 196

[56] References Cited

U.S. PATENT DOCUMENTS

| | | | |
|---|---|---|---|
| 4,238,596 | 12/1980 | Quinn | 528/179 |
| 4,238,597 | 12/1980 | Markezich et al. | 528/179 |
| 4,393,190 | 7/1983 | Tyrell et al. | 528/170 |
| 4,506,065 | 3/1985 | Miller et al. | 528/179 |
| 4,657,977 | 4/1987 | Peters | 528/929 |
| 4,713,439 | 12/1987 | St. Clair et al. | 528/353 |
| 4,757,150 | 7/1988 | Guggenheim et al. | 528/179 |

Primary Examiner—Terressa Mosley-Boykin

[57] ABSTRACT

A process has been surprisingly discovered that can produce a high heat carbonate polymer (i.e., one with a Tg greater that 150° C.), without the drawbacks encountered in attempts to produce a high heat carbonate polymer. The process of the instant invention comprises the steps of:

(1) reacting an aromatic amine with a dihydric phenol to prepare an aminophenol;

(2) reacting an anhydride or dianhydride with the aminophenol to prepare a phenolic precursor; and (3) reacting the phenolic precursor with a carbonate precursor to prepare a high heat carbonate polymer.

18 Claims, 2 Drawing Sheets

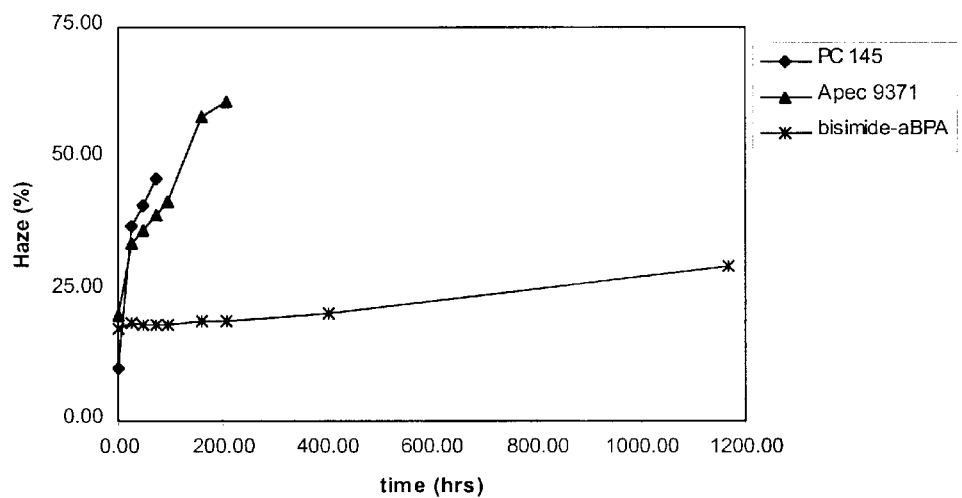
Figure 1: Haze increase of polycarbonate films in caustic at 60°C. Bisimide-aBPA = 14 mol%.

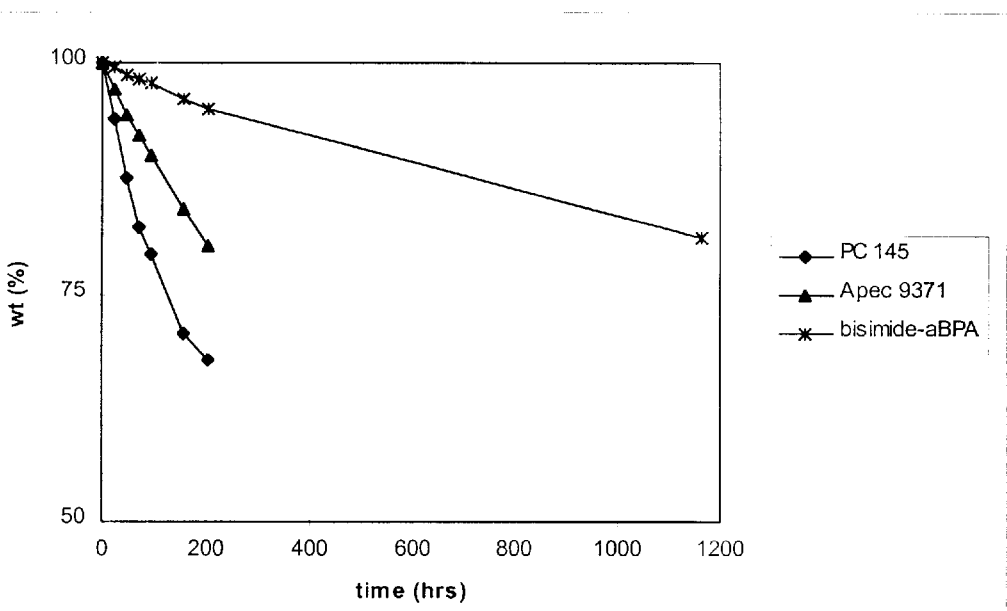
Figure 2: Weight decrease of polycarbonate films in caustic at 60°C. Bisimide-aBPA = 14 mol%.

SYNTHESIS OF PHENOLIC MONOMERS CONTAINING IMIDE OR DIIMIDE MOIETIES AND HIGH HEAT CARBONATE POLYMERS PREPARED THEREFROM

FIELD OF THE INVENTION

This invention relates to synthesis of diphenolic monomers containing imide or diimide moieties and the use thereof to produce high heat polycarbonates. Briefly, this invention relates to an interfacial, melt transesterification or solid state reaction to form a high heat carbonate polymer by employing aminophenols and an anhydride to form a phenolic monomer or precursor containing imide or diimide moieties which phenolic monomer is then reacted with a carbonate precursor such as carbonyl chloride, dialkyl carbonate, diaryl carbonate, alkylaryl carbonate, cycloalkyl carbonate, cycloalkylaryl carbonate, halogen substituted alkyl carbonate or alkoxyto form a high heat carbonate polymer or high heat carbonate copolymer by further reaction thereof with a dihydric phenol.

BACKGROUND OF THE INVENTION

There is a growing need for polycarbonates with a heat of performance greater than commonly obtained with amorphous polycarbonates. Such prior art polycarbonates have a glass transition temperature (Tg) of about 150° C. Because of high heat performance required in today's applications for thermoplastics, a polycarbonate having a higher Tg is wanted while still retaining the same or better optical and mechanical properties as is well known with aromatic polycarbonates.

Several attempts have been made to prepare polycarbonates having a higher heat of performance (i.e. a higher Tg). Recent commercialization of copolymers of bisphenol-A and bisphenol-fluorenone was undertaken but was not successful.

Bi-phenol and (6,6'-dihydroxy-3,3,3',3'-tetramethyl-1,1'-spirobiindane (hereinafter "SBI") have been used along with Bisphenol-A in making polycarbonate with higher Tg. Due to the rigidity and stiffness of the aforementioned comonomers, microcracking of molded parts was a major issue. Furthermore, the high cost of bisphenol and spirobiindane (SBI) raise the cost of polycarbonates prepared therewith.

Consequently, various issues, including deleterious physical properties and/or cost have precluded the commercialization of higher Tg polycarbonates or copolymers.

SUMMARY OF THE INVENTION

A process has been surprisingly discovered that can produce a high heat carbonate polymer (i.e., one with a Tg greater that 150° C.), without the drawbacks encountered in previous attempts to produce a high heat carbonate polymer. The process of the instant invention comprises the steps of:

(1) reacting an aromatic amine with a dihyrdric phenol to prepare an aminophenol;

(2) reacting an anhydride or dianhydride with the aminophenol to prepare a phenolic precursor; and (3) reacting the phenolic precursor with a carbonate precursor to prepare a high heat carbonate polymer. A reaction scheme is shown below:

1) Aromatic Amine+Dihydric Phenol→Aminophenol
2) Anhydride (mono-or di-)+Aminophenol→Phenolic Precursor
4) Phenolic Precursor+Carbonate Precursor→High Heat Carbonate Polymer.

In this process, the aromatic amines are preferably arylamines. The phenolic precursor is preferably a diphenolic precursor. The high heat carbonate polymer may be a high heat polycarbonate, a high heat polycarbonate ester, or a carbonate polymer other than polycarbonate such as polyesters, polyurethanes, hydroxymelamine curing agents or a coating component in acrylic and polyester enamels, cross-linked with hydroxymelamine curing agents or copolymers by further reaction with a dihydric phenol. The high heat polycarbonate and/or the high heat polycarbonate ester may be prepared by an interfacial polymerization process, a melt transesterification process, or a solid state polymerization process, all of which are well known in the prior art.

BRIEF DESCRIPTION OF THE DRAWINGS

FIG. 1 depicts a plot of haze versus time for samples according to the invention and comparative samples exposed to a caustic bath.

FIG. 2 depicts a plot of weight decrease versus time for samples according to the invention and comparative samples exposed to a caustic bath.

DETAILED DESCRIPTION OF THE INVENTION

The synthesis described herein begins with a reaction between an aromatic amine and a dihydric phenol to produce an aminophenol. Next, an anhydride or dianhydride is reacted with an aminophenol to prepare a phenol precursor. Lastly, the phenolic precursor is reacted with a carbonate precursor to form a high heat carbonate polymer.

Preferred aromatic amines for making the aminophenol include arylamines, such as, anline, 2-bromoanline, 2,5-dibromoanline, 2-methylanline, 2-ethylaniline, 2,5-diethylaniline, 2-methoxyaniline, 2,3-dimethoxyaniline, 2-ethoxyanline, 2,3-diethoxyaniline, and the like.

Preferred dihydric phenols for making the amino phenol include, 2,2-bis(4-hydroxyphenyl) propane; 2,2-bis(2,6-dibromo-4-hydroxyphenyl) propane; 3,3-bis(4-hydroxyphenyl) pentane; 2,2-bis(4-hydroxyphenyl) heptane; bis(4-hydroxyphenyl) phenylmethane; 2,2-bis(4-hydroxyphenyl)-1-phenylpropane; and the like.

Upon reacting the aromatic amine with the dihydric phenol, one generates an amino phenol. In the next step of the synthesis, the amino phenol is reacted with a mono or diahydride to produce a phenolic precursor.

The phenolic precursor of this invention is preferably a bisphenol monomer containing imide or diimide moieties.

Preferred aminophenols for preparing the phenolic precursor include those according to formulas 1,2,3, or 4:

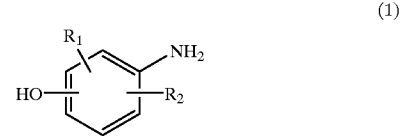

(1)

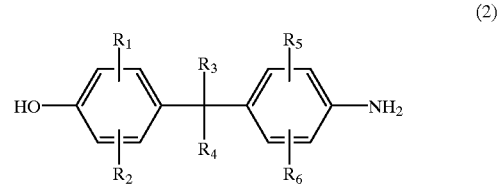

(2)

-continued

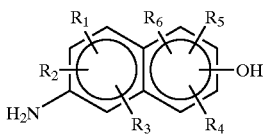
(3)

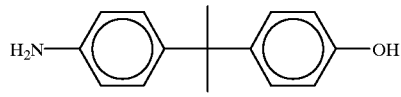
(4)

wherein $R_1$, $R_2$, $R_3$, $R_4$, $R_5$ and $R_6$ of formulas (1) and (3) are independently alkyl, alkylaryl or arylalkyl radicals. The alkyl radical(s) are from is 1–20 carbon atoms, preferably 1–10 carbon atoms and most preferably 1–6 carbon atoms. The aryl radical(s) comprise 1 to 2 aryl radicals. In formula (2), R3 and R4 are independently alkyl radicals of 1 to 4 carbon atoms.

As stated previously, the phenolic precursor of the invention is prepared by reacting an aminophenol with a mono or di-anhydride (collectively "anhydrides"). The following classes of anhydrides according to formulas 5, 6, 7(a) or 7(b) are preferred for synthesizing the diphenolic precursor:

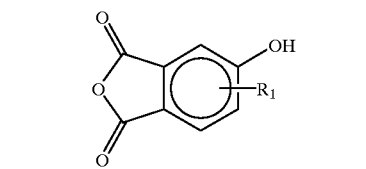
(5)

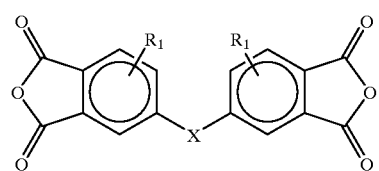
(6)

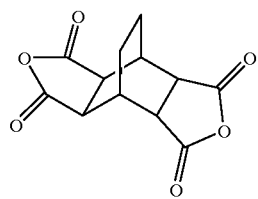
(7a)

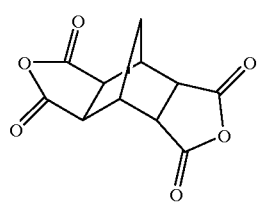
(7b)

In formulas 5 and 6, $R_1$ has the same meaning set forth previously. In formula 6, X is a preferably a bivalent residue of one of the following: bisphenols, substituted bisphenols, substituted Spiro biindane, sulfones, oxygen, or bivalent radicals according to formulas 8–10 below:

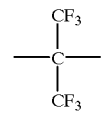
(8)

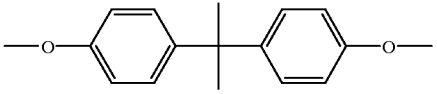
(9)

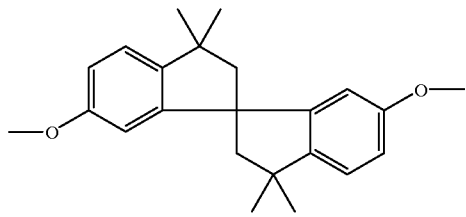
(10)

X may also be the residue (meaning removal of the H atoms from the hydroxyl groups) of the following additional dihydric phenols and substituted dihydric phenols that may be employed to prepare the copolymer of formula (6): (i) dihydroxydiphenyls such as 4,4'-dihydroxydiphenyl methane; 2,2'-dihydroxydiphenyl propane; 2,4'-dihydroxydiphenyl propane; dihydroxynaphthalenes such as 2,6-dihydroxynaphthalene, and the like; (ii) sulfones, such as bis-(4-hydroxyphenyl) sulfone; 2,4'-dihydroxydiphenyl sulfone, 5'-chloro-2,4'-dihydroxydiphenyl sulfone, 5'-chloro-2,4'-dihydroxydiphenyl sulfone; 3'-chloro-4,4'-dihydroxydiphenyl sulfone, and 4,4'-dihydroxytriphenyl disulfone; and (iii) ethers such as 4,4'-dihydroxydiphenyl ether; 4,4'-dihydroxytriphenyl ether; the 4,3'-, 4,2'-, 4,1'-,2, 2'-, 2,3'- dihydroxydiphenyl ethers; 4,4'-dihydroxy-2,6-dimethyldiphenyl ether; 4,4'-dihydroxy-2,5-dimethyldiphenyl ether; 4,4'-dihydroxy-3,3'-dissobutyldiphenyl ether; 4,4'-dihydroxy-3,3'-dissopropyldiphenyl ether; 4,4'-dihydroxy-3,2'-dinitrodiphenyl ether; 4,4'-dihydroxy-3,3'-dichlorodiphenyl ether; 4,4'-dihydroxy-3,3'-difluorodiphenyl ether; 4,4'-dihydroxy-2,3-dibromodiphenyl ether; 4,4'-dihydroxydinaphthyl ether; 4,4'-dihydroxy-3,3'-dichlorodinaphthyl ether; 2,4-dihydroxytetraphenyl ether; 4,4'-dihydroxypentaphenyl ether; 4,4'-dihydroxy-2,6-dimethoxydiphenyl ether; and 4,4'-dihydroxy-2,5-diethoxydiphenyl ether. It should be understood that the above list includes non-limiting examples. Mixtures of the dihydric phenols can also be employed and where dihydric phenol is mentioned herein, mixtures of such materials are considered to be included. X is most preferably a bivalent residue of a bis(4-hydroxyphenyl) alkane in which the central alkane group contains from 1–8 carbon atoms. Especially preferred dihydric phenols are gem-bis(4-hydroxyphenyl) alkanes in which the central alkylidene group contains from 1–8 carbon atoms. Preferably the dihydric phenol is 2,2-bis(4-hydroxyphenyl) propane (i.e., formula 9).

The reaction of the aminophenol and anhydride is generally carried out in an acid medium or a high boiling solvent such as ortho dichloro benzene (ODCB). The reactants are typically heated to reflux temperature for a period of time sufficient to form the phenolic precursor. The solid phenolic precursor is recovered (e.g., by filtration). The recovered phenolic precursor may be further purified by refluxing the phenolic precursor in solvent having a boiling temperature of about 160–200° C., such as ODCB, and subsequently recovering the purified solid phenolic precursor by precipitating the solid product in an organic liquid phase such as xylene.

The phenolic precursor of this invention can be represented by the following formulas:

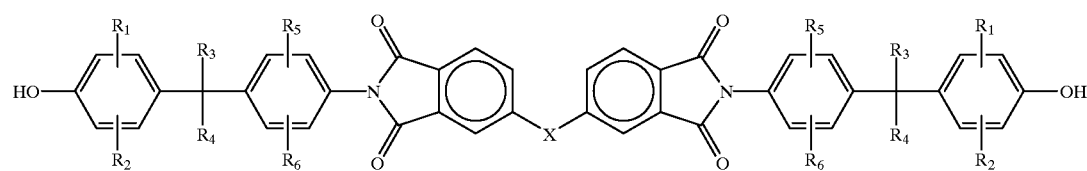

(11)

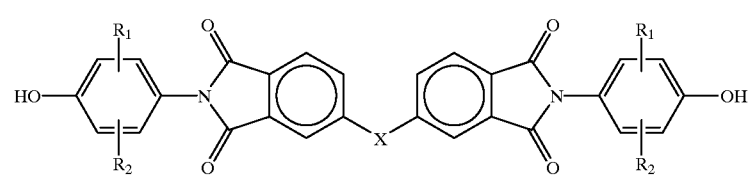

(12)

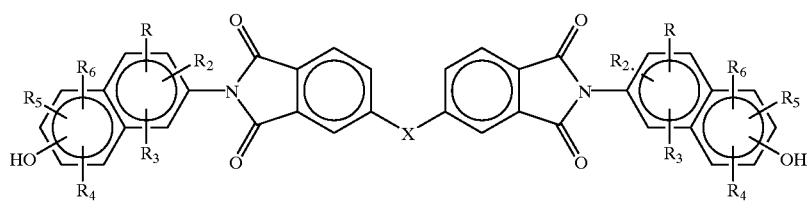

(13)

wherein $R_1$, $R_2$, $R_3$, $R_4$, $R_5$, $R_6$, $R_7$, and $R_8$ are independently selected from alkyl, alkylaryl, and arylalkyl radicals of 1–20 carbon atoms and X is as defined above.

The phenolic precursor utilized in the practice of this invention preferably contains at least two phenolic groups and either 1 or 2 imide moieties. Formulas (11), (12), and (13), show phenolic precursors having two imide groups and two phenolic groups. These compounds are conceptually similar to bisphenol-A (BPA) and, as such, can be used as monomers and comonomers in the preparation of polymeric material such as carbonate polymers.

The phenolic precursor is then reacted with a carbonate precursor such as a carbonyl chloride, dialkyl carbonate, diaryl carbonate, alkyl aryl carbonate, cycloalkyl carbonate, cycloakyl-aryl carbonate, halogen substituted alkyl carbonate or alkoxy carbonate to form a high heat carbonate polymer. This reaction may be performed by an interfacial polymerization process, by reacting the phenolic precursor with a diphenyl carbonate utilizing a melt transesterification process, or by a solid state polymerization process. In yet another reaction scheme, the phenolic precursor and carbonate precursor can be reacted with another dihydric phenol to prepare a high heat carbonate copolymer.

Some preferred polymers made by reacting a phenolic monomer with a carbonate precursor are represented by the following formulas:

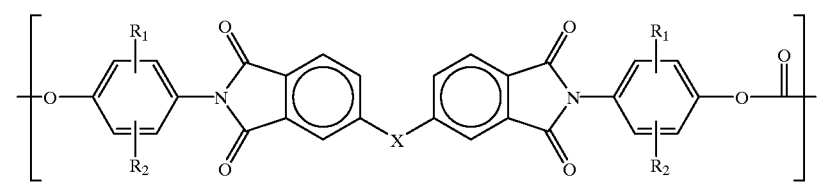

(14)

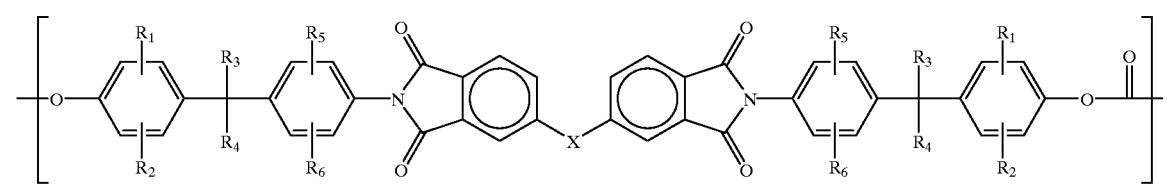

(15)

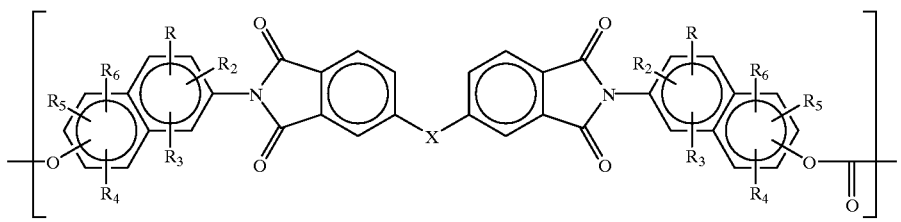
(16)

wherein $R_1$, $R_2$, $R_3$, $R_4$, $R_5$, $R_6$, $R_7$, and $R_8$ have the same meaning as set forth previously and are preferably 1–10 carbon atoms; x has the meaning previously described. The polymers typically have 3 to 100 repeat units.

Alternatively, the phenolic precursor and carbonate precursor can additionally be reacted with another dihydric phenol to form a copolymer wherein the residue of the reactants may be represented by the following general formula:

(dihydric phenol)$_m$ (Formula (11) or (12) or (13))$_y$ wherein m is an integer of 1–100 and y is an integer of 1–100. The dihydric phenols that can be employed herein to form the copolymer can be any of the dihydric phenols described previously herein. The copolymers may be either alternating, random, or block copolymers.

As stated previously, the phenolic precursors of this invention can also be utilized to prepare other high heat carbonate polymers, such as polyestercarbonate and other polymers. The high heat carbonate polymers and copolymers described herein can also be blended with other polymers such as, for example, polyalkyleneterephthalates such as polyethyleneterephthalate (PET) polybutyleneterephalate (PBT), polypropyleneterephthalate (PPT), poly(ethylenenaphthanoate) (PEN), polybutylenenapthanoate (PBN), polyethesinile, polyesterimide and the like; acrylonitrile-butadine-styrene (ABS), and other polymers which are compatible with the carbonate polymer.

In addition, the phenolic precursor may be utilized in preparing copolyestercarbonates as disclosed in U.S. Pat. No. 4,506,065, which is incorporated herein by reference. The copolyestercarbonates and copolyester carbonate imide and the like can include blends thereof with other polymers that are compatible with such copolyestercarbonates. These may include such other polymers as set forth above such as polyesters, ABS, and the like.

The aromatic copolyestercarbonates suitable for use in the present invention are derived from carbonate precursors and dihydric phenol which are also useful in the preparation of a comparable aromatic polycarbonate. However, more that one appropriate dihydric phenol, as discussed above, may be used to prepare copolyestercarbonates of the invention. The aromatic dicarboxylic acid employed in the preparation of the copolyester carbonate is preferably terephthalic acid or mixtures of isophthalic and terephthalic acid and may be for example, of the following formula:

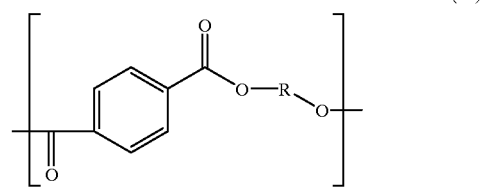
(17)

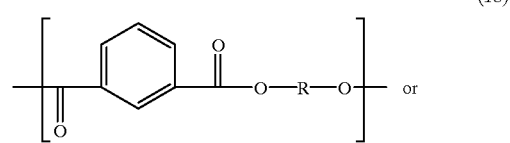
(18)

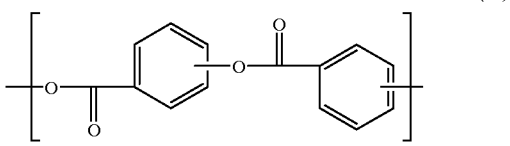
(19)

wherein R is an alkyl, arylakyl or alkylaryl radical of 1–20 carbon atom and the molecule has 1–100 repeat units. Any ester forming derivative of a carboxylic acid which is reactive with the hydroxyl of a dihydric phenol may be employed. The acid halides are generally employed because of their ease of reactivity and availability. The acid chlorides are preferred.

The ester content of the aromatic copolyestercarbonate should preferably be in the range from about 20 to about 50 mole percent, and more preferably from about 25 to about 45 mole percent. In another preferred emobdiment, the aromatic copolyestercarbonate comprises a mixture of isophthalic and terephthalic acids in a ratio of from about 0.1:9.9 to 3:7 isophthalic to terephthalic acid. A more preferred ratio is from about 0.5:9.5 to 2:8.

The standard methods for preparing copolyestercarbonate can be employed. Such methods are found, for example in U.S. Pat. Nos. 4,238,596 and 4,238,597, which are incorporated herein by reference.

In addition, the diphenolic precursor of this invention may be utilized to prepare other polymers compositions such as polyesters, polyurethane, coating compositions in acrylic and/or polyester enamels cross-linked with a hydroxymelamine cross-linking agent.

Additionally, various other additives may be employed with the polymers of this invention. Specifically, the polymers according to the invention may further contain other resins and additives such as pigments, UV-stabilizers, reinforcing agents, fillers, impact modifiers, heat resisting agents, antioxidants, anti-weathering agents, heat stabilizers, mold release agents, lubricants, nucleating agents, plasticizers, flame retardants, flow-improving agents and anti-statics. These additives may be introduced in a mixing or molding process, provided the properties of the composition are not damaged.

Any type of pigment that is well known for inclusion in thermoplastic materials can also be added to the polymer. Preferred pigments include titanium dioxide, zinc sulfide, carbon black, cobalt chromate, cobalt titanate, cadmium sulfides, iron oxide, sodium aluminum sulfosilicate, sodium sulfosilicate, chrome antimony titanium rutile, nickel antimony titanium rutile, zinc oxide, and polytetrafluoroethylene.

It may also be advantageous to include various chemicals to prevent degradation of the polymer due to exposure to UV light (hereinafter "UV stabilizers"). Suitable UV stabilizers include substituted benzotriazoles, or triazines, or tetraalkylpiperidines. The UV stabilizers may be mixed into the thermoplastic matrix, or they can be included only in a "hardcoat" transparent protective layer which is applied over the viewing surface.

The optional reinforcing fillers may be metallic fillers such as fine powder aluminum, iron, nickel, or metal oxides.

Non-metallic fillers include carbon filaments, silicates such as mica, aluminum silicate or clay, talc and asbestos, titanium oxide, wollastonite, novaculite, potassium titanate, titanate whiskers, glass fillers and polymer fibers or combinations thereof. Glass fillers useful for reinforcement are not particularly limited in their types or shapes and may be, for instance, glass fibers, milled glass, glass flakes and hollow or solid glass beads. Glass fillers may be subjected to surface treatment with coupling agents such as silane or titanate-type agents to enhance their adhesion with resin, or coated with inorganic oxides to provide some surface color to the filler.

Reinforcing fillers are preferably used in an amount sufficient to yield the reinforcing effect, usually 1 to 60% by weight, preferably less than 10% by weight, based on the total weight of the composition. Glass fibers, or a combination of glass fibers with talc, mica or aluminum silicate are preferred reinforcing agents.

Phosphites (e.g., aromatic phosphite thermal stabilizers), metal salts of phosphoric and phosphorous acid, hindered phenol antioxidants, and aromatic lactone radical scavengers may also be added as stabilizers or antioxidants.

Suitable antistatic agents include, but are not limited to, phosphonium salts, polyalkylene glycols, sulfonium salts and alkyl and aryl ammonium salts.

Suitable mold release agents include, but are not limited to, pentaerythritol tetracarboxylate, glycerol monocarboxylates, glycerol tricarboxylates, polyolefins, alkyl waxes and amides.

DETAILED DESCRIPTION OF THE EXAMPLES

This invention can be further described by means of the following examples. It is understood, however, that this invention shall in no way be restricted by these examples. Where amounts are in terms of percent, they are percent by weight unless otherwise stated.

EXAMPLE 1

Synthesis of a Bisphenol Diimide Oligomer

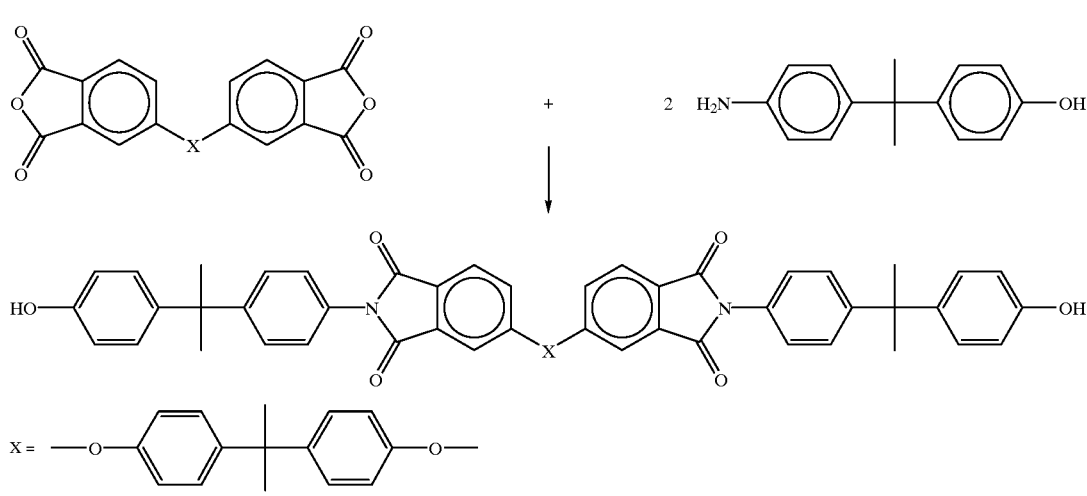

(20)

Method A:

A three liter, four neck flask equipped with an overhead stirrer, a thermometer, a condenser, an argon inlet and outlet, was charged with: −104.10 grams of BPA-dianhydride (200 mmol.) from the Ultem plant −93 grams of 2-(4-Aminophenyl)-2-4'-Hydroxyphenyl)-propane (96%), and −1000 ml of glacial acetic acid.

The resulting mixture was refluxed for 16 hours under a flow of argon. By the time reflux started, all the reactants had passed into solution and no precipitation was observed throughout the reflux period. After 16 hours, the reaction was cooled to room temperature and quenched by pouring the reaction mixture into two 4L beakers each filled with water. A white precipitate formed. After stirring, the precipitate was isolated by filtration. The precipitate was then oven dried at 50° C. The dried crystals were further purified by refluxing in 500 mL of ODCB for about 5 hours, subsequently reprecipitating by the crystals adding 100 mL of Xylene. The crystal composition was confirmed by $^1$H, $^{13}$C NMR.

Method B:

A 500 ml three-neck flask equipped with a mechanical stirrer and condenser was charged with 20 g (0.088 mol) of amino-BPA, 22.9 g (0.044 mol) of BPA dianhydride, 160 g of OBCB, 10.7 g of toluene, and 330 ppm triethyl amine. The flask was then purged with nitrogen and the reaction mixture heated to 130° C. and allowed to stir for 2 hours. An additional 10 ml of toluene was then added and the reaction allowed to continue for an additional 2.5 hours.

The macromer was precipitated by adding 30 g of O-xylene while allowing the reaction mixture to cool. The macromonomer was filtered and dried at 50° C. for 10 hours. This product was soluble in tetrahydrofuran (THF), anisole, ODCB, dimethyl sulfoxide (DMSO), acetonitrile, and warm chlorobenzene. It was insoluble in diethyl ether, chloroform, and methylenechloride.

mixture was allowed to stir at 130° C. for a period of 4.5 hours, under nitrogen atmosphere, after which the temperature was reduced to room temperature. 500 ml of cold methanol was then added to the reaction mixture to crystallize the product. This mixture was allowed to stir for 30 minutes. The crystals were then recovered by filtration, added to 400 ml of cold methanol, and allowed to stir an additional 30 minutes. The product was then filtered again, and dried invacuoat 75° C. for approximately 20 hours. This reaction is represented below. Bisphenol Diimide

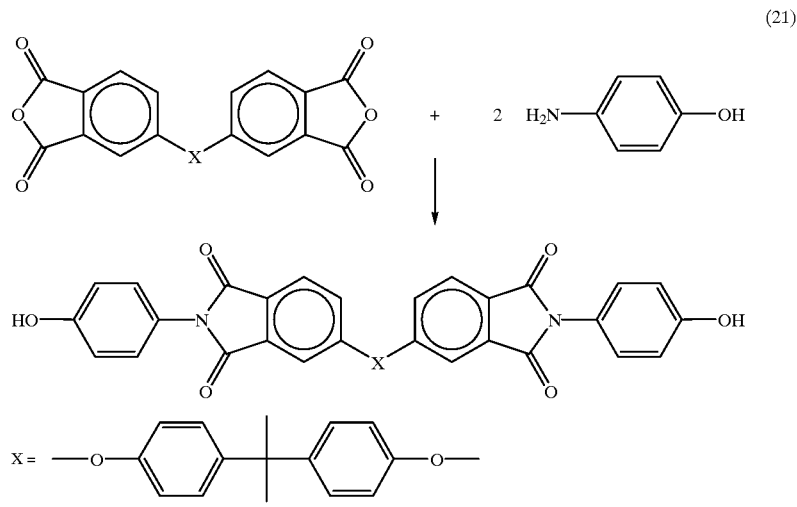

(21)

An alternative "melt" route polymerization was as follows. A 100 ml three-neck flask equipped with a mechanical stirrer and condenser was charged with 11.45 g (0.050 mol) BPA dianhydride and 10.0 g (0.044 mol) amino-BPA. This mixture was then heated to 200° C., and allowed to react for 1 hour under a nitrogen blanket. The product was then cooled and ground into a fine powder.

EXAMPLE 2

Synthesis of a Bisphenol Diimide Oligomer

A 1000 nml three-neck flask equipped with a mechanical stirrer and condenser was charged with 80.298 g (0.154 mol) of BPA dianhydride, 33.66 g (0.308 mol) of 4-aminophenol, and 400 ml of acetic acid. The mixture was then purged with nitrogen and allowed to react for a period of 10 hours at 125° C. under continuous stirring. The reaction product was the poured into an excess of warm water (2L) and stirred for 30 minutes with a magnetic stirrer. The resulting macromer crystals were filtered, and subsequently washed with water until the pH was 6.6. The crystals were then washed with cold methanol to facilitate drying, and dried in-vacuoat for approximately 8 hours at 75° C. The product was soluble in DMSO, hot ODCB, and THF. The product was insoluble in toluene, water, methanol, and methylene chloride In an alternative reaction, a flask equipped with a mechanical stirrer and condenser was charged 40.148 g (0.771 mol) BPA dianhydride, 16.83 g (0.154 mol) 4-aminophenol, 200 ml of ODCB, 25 ml of toluene (to remove reaction product), and 0.5 ml of triehtyl amine. The

EXAMPLE 3

Synthesis of a Bisphenol Diimide Oligomer

A 250 ml three-neck flask equipped with a mechanical stirrer and condenser was charged with 12.97 g (0.0586 mol) of pyromellitic dianhydride, 12.79 g (0.1172 mol) of 3-amino phenol, and 100 ml of dimethyl acetamide. The mixture was allowed to react for approximately 20 hours under nitrogen atmosphere. 22.6 ml (0.2344 mol) of acetic anhydride was then added, and the reaction temperature was increased to 80° C. for a period of 5 hours. The resulting suspension was then cooled to room temperature and filtered. The product was washed with 10 ml of dimethyl acetamide and 70 ml of methanol. The product was dried in-vacuo at 75° C. for 7 hours. The macromonomer was yellow, and soluble in hot DMSO and NaOH solution. It was insoluble in THF, water, methylene chloride, and ODCB.

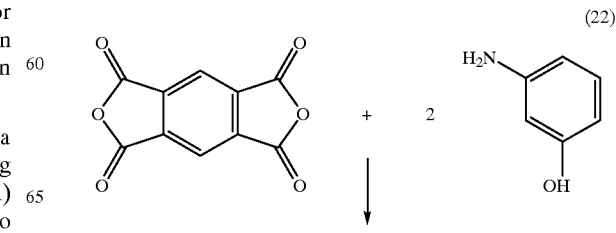

(22)

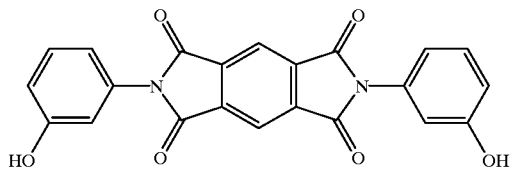

EXAMPLE 4

Polymerizing the Bisphenol Diimide Oligomer of Example 1

A small polymerization reactor was charged with 39.99 g of polycarbonate prepolymer having a MW=7400, MN=2400, phenol 0.193%, diphenyl carbonate(DPC) 0.317%, and BPA 0.067%, 12.05 g of the oligomer prepared in Example 1, and 3.004 g of DPC. The mol ratio of DPC to bisphenol diimide was 1.10:1.0. After the reactor was charged, the contents were purged with nitrogen for a period of 10 minutes. Vacuum was the applied for a period of 5 minutes followed by a nitrogen flush. In the first reaction stage, the reactor contents were melted under a nitrogen atmosphere at 200° C. for 10 minutes. In the second stage of the reaction, the pressure was decreased to approximately 70–80 mbar, and the melt temperature increased to 210° C. During this second stage, stirring was maintained at 30 rpm. After 40 minutes, we started the third reaction stage by decreasing the pressure to approximately 10 mbar, and increasing the melt temperature to 270° C. Stirring was maintained at 30 rpm for 50 minutes. The fourth and final reaction stage was accomplished by reducing the pressure to 0.2–0.8 mbar and rasing the melt temperature to 300° C. The reaction mixture stirred for an additional 20 minutes during this stage. The resulting molten polymer was then removed from the reactor and allowed to cool. The polymer had a MW of 49,800, MW/MN=2.7, and a Tg of 169° C. The formula for this polymer is shown below:

|  | MW via PC calibration | Tg (° C.) |
|---|---|---|
| % Example 1 | | |
| 15 | 39,000 | 159.8 |
| 25 | 49,800 | 168.5 |
| 30 | 51,000 | 169.3 |
| 48 | 48,000 | 175.0 |
| % Example 3 | | |
| 25 | 37,800 | 171.0 |

EXAMPLE 6

A. Polymerization by the Melt Process

The Pyrex glass reactors used for this synthesis were acid washed (soaked during 24 hours in 1 N HCl solution) and rinsed extensively with milli-Q water to eliminate trace surface contamination which is essential for melt transesterification polymerization.

Polyetherimide-PC copolymers made from BPA-bisimide-3-aminophenol and BPA (40 wt% BPA; 60 wt% BPA-bisimide-3-aminophenol) were synthesized by the following procedure. First, BPA-PC prepolymer (Mw(PC)= 7400 g/mol; 10.77 g; 0.0421 mol; contains 2.10E-8 mol NaOH), BPA-bisimide-3-aminophenol (14.5 g; 0.0207 mol) and diphenylcarbonate (4.87 g; 0.0228 mol) were charged into a dry glass reactor. No extra catalysts (NaOH/TMAH) were added. The reactor was deoxygenated by evacuating to 0.5–1 mbar, and subsequently re pressurizing with nitrogen to atmospheric pressure. This was repeated four times. Next, the reactor was electrically heated to 230° C. to receive a homogeneous melt. Once a small amount of the mixture was melted (under nitrogen atmosphere), stirring was started carefully to accelerate melting (final stirring speed 40 rpm). Total melting time was 1 hour. Then the pressure was slowly decreased to 90 mbar. After 30 minutes, the temperature was (23)

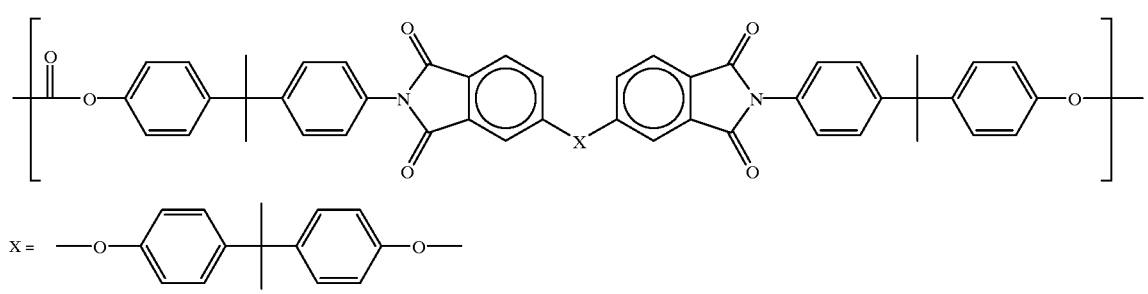

Example 5

Perparing Different Polymers

This example repeats the same polymerization procedure as Example 4, but use differing amounts of the bisphenol diimide of Example 1. Also, the bisphenol diimide oligomer of Example 3, was polymerized. The following results were obtained:

raised to 285° C., pressure was further decreased to 40 mbar, and phenol started to distill. Phenol continued to distill during the next 30 minutes into the cold trap (cooled with liquid nitrogen). The reaction temperature was then raised to 300° C. At this time, the vacuum was decreased further to 7 mbar, and held there for 20 minutes. Next, reactor pressure was lowered to 1 mbar. After another 20 minutes, maximum vacuum was applied (0.1–0.4 mbar), and the temperature was raised to 310° C. Polymerization was continued for 1 hour. A total of 3.5 grams of distillate was collected during the course of the reaction. A clear, transparent, ochreous polycarbonate was obtained, yielding the following analytical data: Mw(PC)=20500 g/mol; Mn(PC)=7700 g/mol; Mw/Mn=2.7; Tg=163° C. (20° C./min).

This procedure was also used to synthesize the following copolymers:

- Polyetherimide-PC copolymers made from BPA-bisimide-4-aminophenol and BPA (55 wt% BPA; 45 wt% BPA-bisimide-4-aminophenol), Mw(PC)=35400 g/mol; Mn(PC)=14700 g/mol; Mw/Mn=2.4; Tg=174° C.;
- Polyetherimide-PC copolymers made from BPA-bisimide-aminoBPA and BPA (60wt % BPA; 40 wt % BPA-bisimide-aminoBPA), Mw(PC)=24000 g/mol; Mn(PC)=10500 g/mol; Mw/Mn=2.3; Tg=165° C.;
- Polyetherimide-PC copolymers made from BPA-bisimide-ethanolamine and BPA (53 wt % BPA; 47 wt % BPA-bisimide-ethanolamine), maximum reactor temperature was 270° C., Mw(PC)=27100 g/mol; Mn(PC)=10000 g/mol; Mw/Mn=2.7; Tg=138° C.;
- Polyetherimide-PC copolymers made from PMDA-bisimide-ethanolamine and BPA (69 wt % BPA; 31 wt % PMDA-bisimide-ethanolamine), maximum reactor temperature was 270° C., Mw(PC)=29000 g/mol; Mn(PC)=8300 g/mol; Mw/Mn=3.5; Tg=155° C.

B. Polymerization by the Interfacial Process

Polyetherimide-PC copolymers made from BPA-bisimide-amino BPA and BPA (60 wt % BPA; 40 wt % BPA-bisimide-aminoBPA) were synthesized by the following procedure. BPA-bisimide-amino BPA (22.5 g; 0.0240 mol), BPA (27.5 g; 0.121 mol), p-Cumylphenol (0.982 g; 0.00463 mol), Sodium Gluconate (1.5 g; 0.00688 mol), Triethylamine (0.18 g; 0.00178 mol), 138 g distilled water, 430 g methylene chloride and 5 g 32 wt % NaOH (aq) were added to a 1 liter 3-neck round flask. The mixture was stirred at 25° C. and the initial pH was 11.5. The mixture was phosgenated for 30 minutes. The mixture temperature raised to 40° C. (reflux temperature of methylenechloride) during the reaction due to the reaction exotherm, and pH was kept as close as possible to about 9–10 by simultaneously adding caustic solution. In total, 34.8 g of phosgene (0.35 mol) was added. Next, the pH was brought back to 11.5, and after phase separation, the water phase was discarded. Then, the organic phase was washed once with acid solution, and several times with water.

A clear, transparent, slightly colored polycarbonate was obtained, yielding the following analytical data: Mw(PC)= 32300 g/mol; Mn(PC)=7600 g/mol; Mw/Mn=4.3; Tg=166° C.

This procedure was also applied to make the following copolymer:

- Polyetherimide-PC copolymers made from BPA-bisimide-4-aminophenol and BPA (60 wt % BPA; 40 wt % BPA-bisimide-4-aminophenol), Mw(PC)=33100 g/mol; Mn(PC)=10800 g/mol; Mw/Mn=3.1; Tg=168° C.

The compositions of all the copolymers was determined with nitrogen analysis and by $^{13}C$ NMR. There was a good agreement between experimental and calculated amounts of the bisimide incorporated. NMR studies revealed some blockiness in the interfacial copolymers whereas the melt copolymers are completely random.

EXAMPLE 7

Hydrolytic Stability/Autoclave Test

Tests were performed on injection molded plaques. The plaques were placed in an autoclave which is operated at 120° C. and 1.2 bar. Haze and Mw (GPC) were measured on several stages during autoclaving.

Chemical Resistance

Transparent polymer films of 15 micron thickness were obtained by hot pressing (2 minutes, 250–300° C., 5 ton) polymer granules. The films were immersed in a 1.8 wt % NaOH solution in an oven at 60° C. Haze, yellowness index and transmission (according to ASTM D1003 and D1925) and weight were determined after rinsing the samples with distilled water and isopropanol.

The results of the caustic test for the bisimide copolymers are depicted in FIGS. 1 and 2. Polymers PC145 (conventional BPA polycarbonate) and Apec 9371 (high heat polycarbonate commercially available from Bayer) are given as comparative examples. Haze was by far the best property to distinguish between the different samples. Most polymers showed a large increase in haze in the first 3–4 days. Both of the control samples dissolved after a few days (max. 10 days). Regular BPA-PC films, for example, dissolved completely within 5 days. Only the bisimide copolymers remained unchanged. The total haze increase of the BPA-bisimide-amino-BPA copolymer was only 12% (from 18 to 30%) after 1166 hours, whereas the weight loss was only 19%.

Other bisimide samples were even tested up to 1581 hours (~66 days) and showed only a 19% increase in haze. GPC measurements revealed that the Mw was unchanged after 1581 hrs. These results are very surprising in that only 14 mol % bisimide units are incorporated in the copolymer. Thus one would expect that the copolymers behave more like regular PC. Calculations showed also that the number of carbonate linkages in a polymer chain of PC 145 and in Apec 9371 was almost equal to the number of carbonate linkages in the bisimide-aBPA copolymers. Despite this the bisimide copolymers have a very good resistance against caustic compared to BPA-PC as shown in FIGS. 1 and 2.

During the autoclave tests, the bisimide copolymers showed the same behavior as regular polycarbonate with respect to molecular weight decrease and haze increase (only the initial values of haze and Mw were different). (See FIG. 2) In fact, these results are very encouraging as the bisimide copolymers still contain active catalyst (NaOH), which is believed to play an important (catalytic) role during hydrolysis of carbonate bonds. The reference samples (PC145 and PC175) were prepared via the interfacial polymerization process, and therefore do not contain active catalyst species.

A striking feature, however, was the presence of white spots on all BPA-PC plaques after appr. 100 hrs. This is believed to be pure BPA resulting from degradation. Only the bisimide copolymers did not show these white spots. In the course of the experiment the plaques also became sticky (lowering of Tg because of decrease of Mw) except for the bisimide copolymers.

While many modifications and variations of the present invention are possible in view of the foregoing specification, it is understood that they would fall within the scope of the appended claims.

What is claimed is:

1. A phenolic precursor prepared by reacting an aminophenol and an anhydride wherein said aminophenol is selected from the group consisting of:

(1)
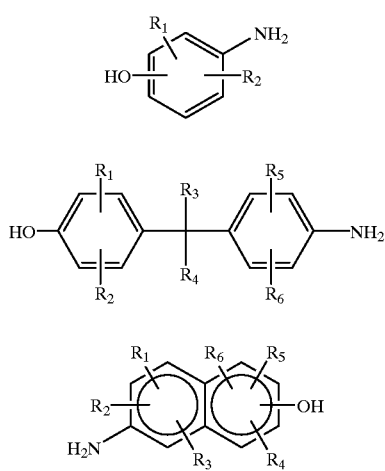

(2)

(3)

wherein $R_1$, $R_2$, $R_3$, $R_4$, $R_5$, and $R_6$ are independently selected from alkyl, alkylaryl and arylalkyl radicals of 1–20 carbon atoms, and said anhydride is selected from the group consisting of:

(5)

(6)

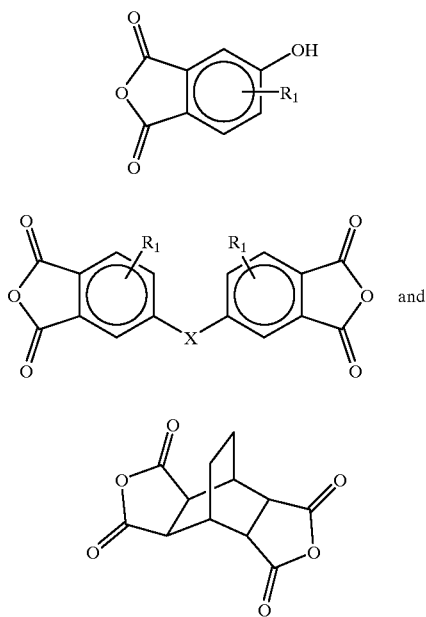

and (7a)

(7b)

wherein X is a residue independently selected from the group consisting of dihydric phenols, substituted dihydric phenols, spiro biindanes, sulfones, oxygen, and the following bivalent radicals:

(8)
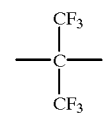

(9)
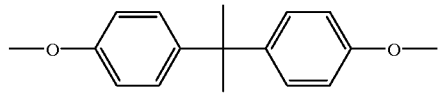

(10)
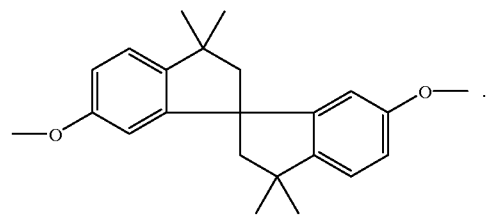

2. The phenolic precursor of claim 1, wherein the phenolic precursor is the residue of the reaction of formula (1) and (5) of claim 1.

3. The phenolic precursor of claim 1 wherein the phenolic precursor is the residue of the reaction of formula (2) and (5) of claim 1.

4. The phenolic precursor of claim 1, is the residue of the reaction of formula (3) and (6) of claim 1.

5. A high heat carbonate polymer which is the residue a reaction of a phenolic precursor of claim 1 and a carbonate precursor.

6. The high heat carbonate polymer of claim 5, wherein the carbonate precursor is carbonyl chloride.

7. A high heat carbonate polymer which comprises repeating units having a formula selected from the group consisting of:

(14)
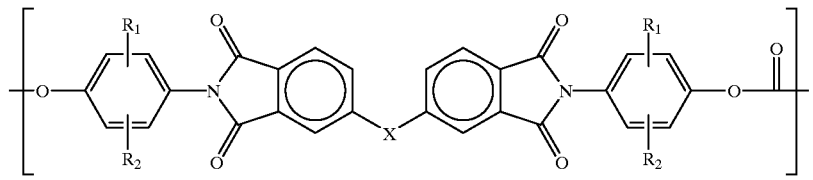

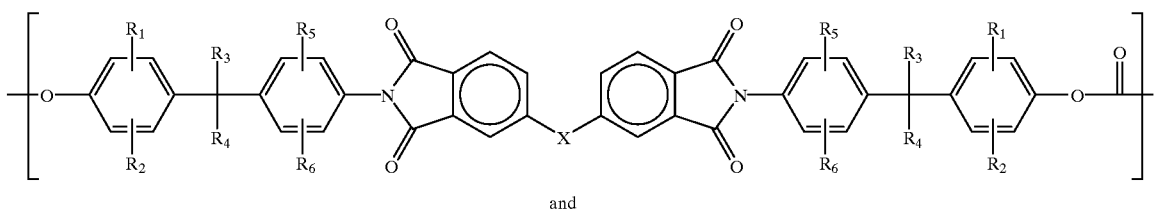

(15)

and

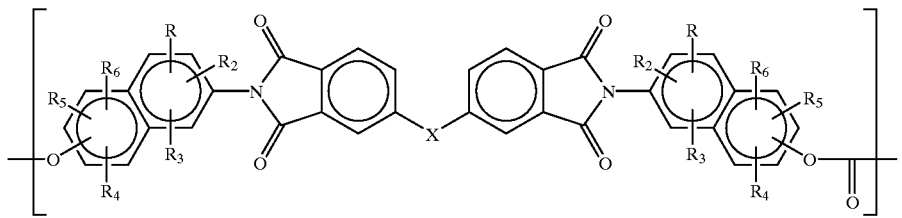

(16)

wherein $R_1$–$R_6$ are independently selected from the group consisting of alkyl, alkylaryl and arylalkyl radicals of 1–20 carbon atoms, and X is independently selected from the group consisting of dihydric phenols, substituted dihydric phenols, spiro biindanes, sulfones, oxygen, and the following bivalent radicals:

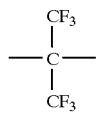

(8)

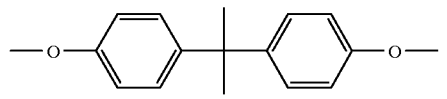

(9)

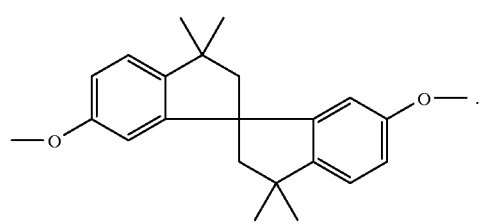

(10)

8. A high heat carbonate polymer which is the residue of the reaction of a phenolic precursor of claim 1, a dihydric phenol and a carbonate precursor.

9. A process comprising the steps of (1) reacting a dihydric phenol with an aromatic amine to form an aminophenol, (2) reacting the aminophenol with an anhydride in an acid medium or high boiling temperature solvent at reflux temperature to form a phenolic precursor.

10. The process of claim 9 where in the aminophenol is reacted with the anhydride reaction at reflux temperature for about 10 to 16 hours.

11. The process of claim 9, wherein the phenolic precursor is purified by refluxing in a high boiling temperature solvent having a boiling temperature of about 160 to about 200° C., and then recovering purified solid diphenolic precursor by precipitating in an organic liquid phase.

12. The process of claim 11, wherein the high boiling solvent is ortho dichloro benzene.

13. The process of claim 11, wherein the organic liquid phase is xylene.

14. A process according to claim 11, which further comprises the step of (3) reacting the phenolic precursor with a carbonate precursor in the presence of an amine catalyst by an interfacial polymerization process, and then recovering the carbonate polymer in solid form.

15. The process of claim 14, wherein the carbonate precursor is diphenyl carbonate, and the process of forming the high heat carbonate polymer is a melt transesterification process.

16. The high heat carbonate polymer of claim 7, which further compreises a copolymer, wherein the distribution of the copolymer is random, alternating block or a mixture thereof.

17. The carbonate copolymer of claim 16, wherein the copolymer has a glass transition temperature greater than 150° C.

18. A phenolic precursor selected from the group consisting of:

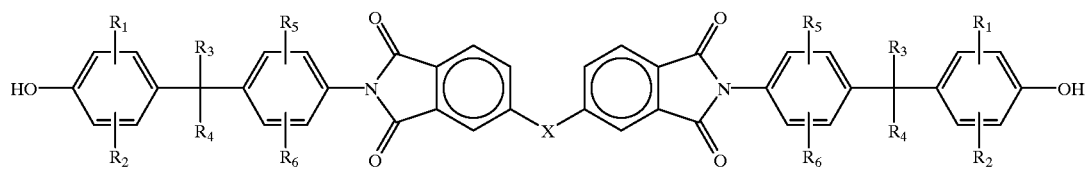

(11)

(12)
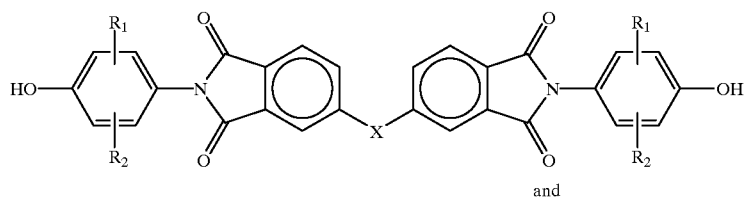
and
(13)
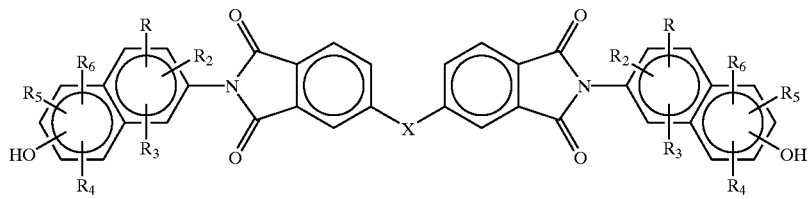
wherein $R_1$ to $R_6$ are independently selected from the group consisting of alkyl, alkylaryl and arylalkyl radicals of 1–20 carbon atoms, and X is independently selected from the group consisting of dihydric phenols, substituted dihydric phenols, spiro biindanes, sulfones, oxygen, and the following bivalent radicals:
(8)
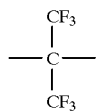
-continued
(9)
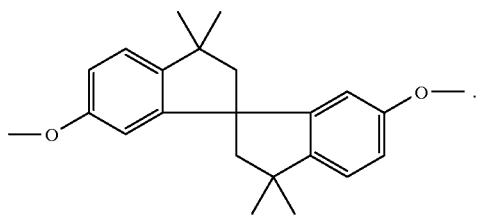
(10)
* * * * *